United States Patent [19]
Bishop

[11] Patent Number: 5,121,743
[45] Date of Patent: Jun. 16, 1992

[54] HAND RESTRAINING DEVICE

[75] Inventor: Bonnie L. Bishop, Albuquerque, N. Mex.

[73] Assignee: Chester Ingier, Downey, Calif.

[21] Appl. No.: 622,929

[22] Filed: Dec. 6, 1990

[51] Int. Cl.⁵ .................................................. A61F 5/04
[52] U.S. Cl. ...................................... 602/22; 128/879; 602/21
[58] Field of Search ............... 128/77, 83, 87 A, 878, 128/879, 880, 877, DIG. 15, DIG. 19; 132/73; 2/16

[56] References Cited

U.S. PATENT DOCUMENTS

| | | | |
|---|---|---|---|
| 1,708,758 | 4/1929 | Freileweh | 128/87 A |
| 2,335,290 | 11/1943 | Medaris | 272/126 X |
| 2,450,298 | 9/1948 | Peterson et al. | 128/DIG. 19 X |
| 3,198,197 | 10/1965 | Van Halanger | 132/73 |
| 3,476,108 | 11/1969 | Matukas . | |
| 3,581,740 | 6/1971 | Sherbourne | 128/87 A X |
| 3,724,456 | 4/1973 | Waxman | 128/877 |
| 3,776,225 | 12/1973 | Lonardo | 128/DIG. 15 |
| 3,788,307 | 1/1974 | Kistner | 128/77 |
| 4,127,120 | 11/1978 | Applegate | 128/DIG. 15 X |
| 4,254,766 | 3/1981 | Kordis | 128/877 |
| 4,370,976 | 2/1983 | Wanchik et al. | 128/77 |
| 4,674,110 | 6/1987 | Eaton et al. | 128/77 X |
| 4,698,850 | 10/1987 | Patton, Sr. et al. | 2/159 |

FOREIGN PATENT DOCUMENTS

| | | | |
|---|---|---|---|
| 1131756 | 2/1957 | France | 128/879 |
| 2501037 | 9/1982 | France | 128/77 |
| 8302022 | 1/1985 | Netherlands | 128/878 |

Primary Examiner—Gene Mancene
Assistant Examiner—L. Thomas
Attorney, Agent, or Firm—DeWitt M. Morgan

[57] ABSTRACT

A hand restraining device including a rigid support member and a plurality of straps for securing the hand, fingers and, preferably the wrist and forearm of an individual to such support member. The support member includes a hand, wrist and forearm portions and three finger portions. A rigid knuckle restraining piece is also included to prevent the user from bending his/her knuckles. Except for the wrist strap, each strap is, at one end, secured to an elongated slot provided in the support member which permits lateral positioning of the strap along the length of the support member. The opposite end of each strap is secured to the back surface of the support member by a Velcro fastener or equivalent.

4 Claims, 2 Drawing Sheets

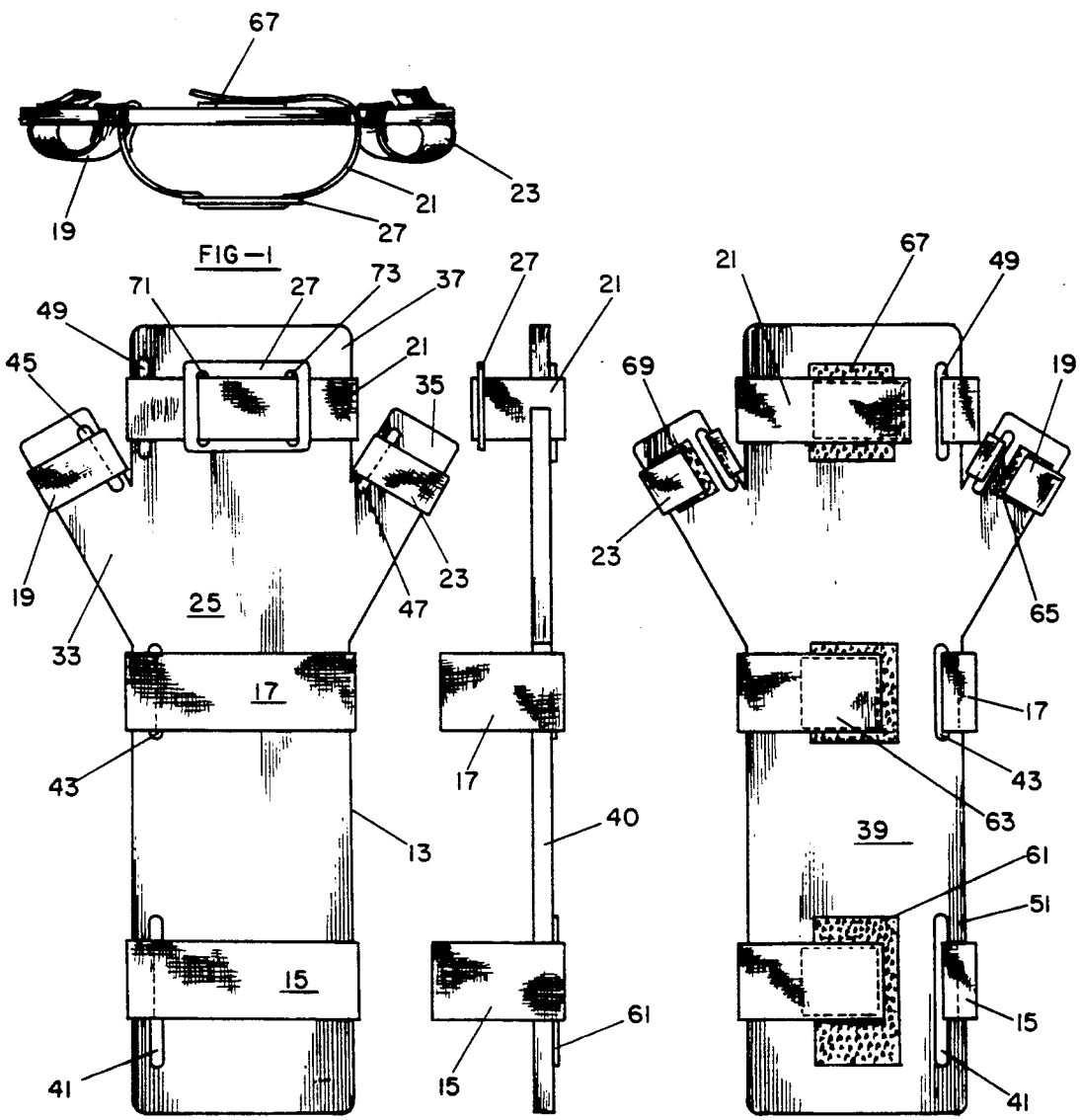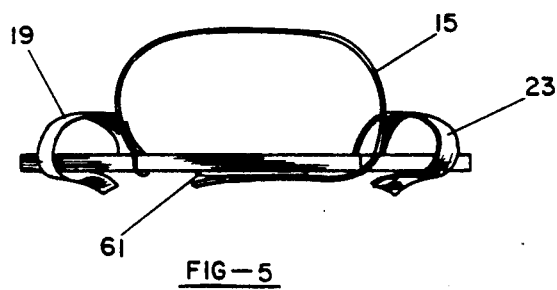

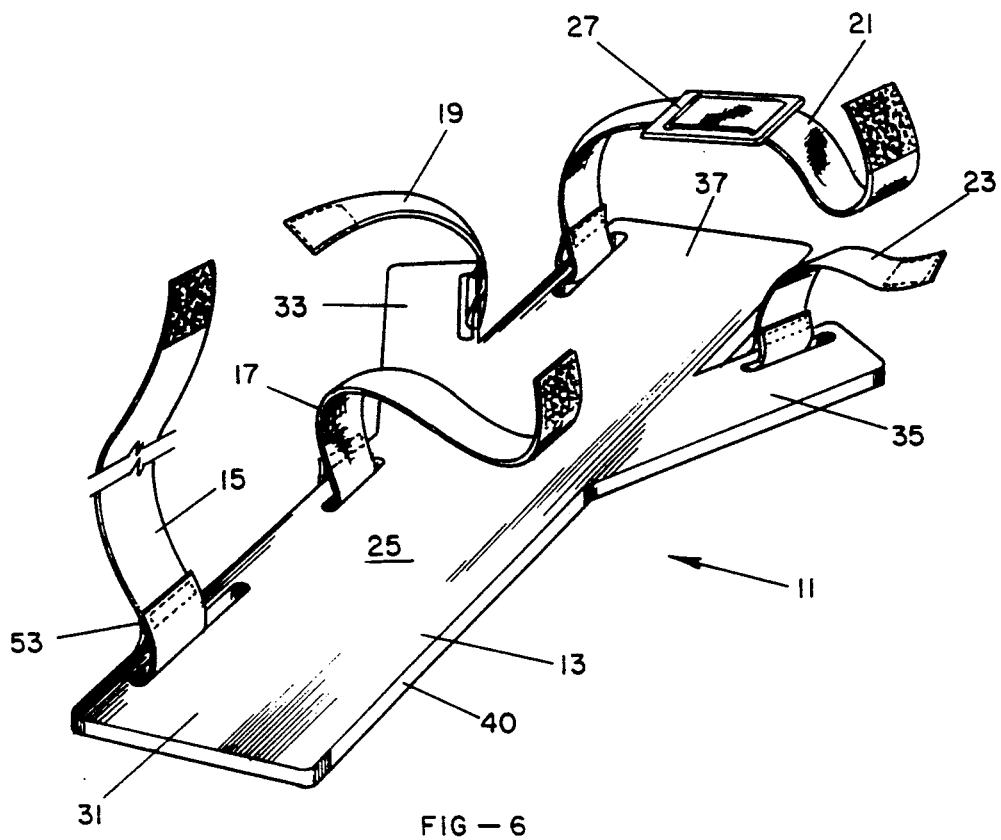
FIG—6
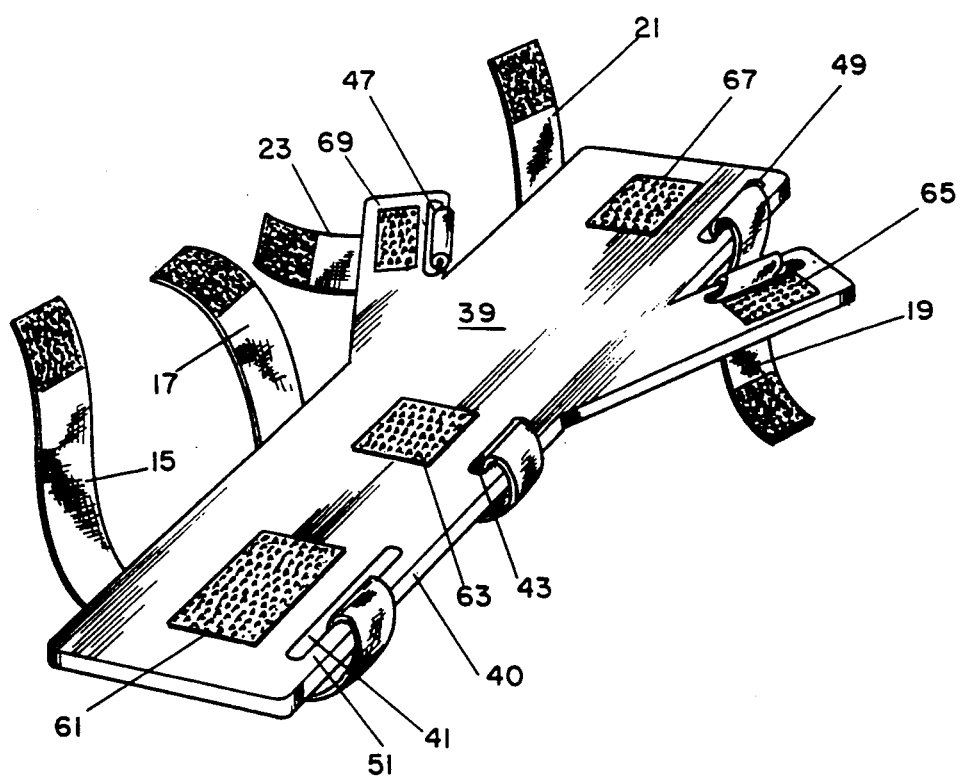
FIG—7

HAND RESTRAINING DEVICE

BACKGROUND OF THE INVENTION

This invention pertains to the field involving treatment of the human body and, more specifically, to apparatus for the restraint of an infant's (or toddler's) hand in such a manner that the infant's fingernails are exposed for easy and convenient clipping, trimming etc.

In hospitals or other similar institutions or locations, there is a need for hand restraints to be used upon uncooperative or confused patients to prevent them from scratching or removing, for instance, catheters or intervenous tubes. One such device is disclosed in U.S. Pat. No. 3,476,108 to A. G. Matukas, which discloses a hand restraint in the form of a flexible fiberglass glove that folds with the user's hand and can be fastened in a fist shape to retain the hand in the position as illustrated in FIG. 3 of this reference. Matukas, in his "Background of the Invention", also discloses other prior art devices.

Applicant is also aware of U.S. Pat. No. 4,698,850 to E. E. Patton, Sr., et al., which discloses a glove for use by persons taking therapeutic exercises involving use of such person's hands. The device includes a plurality of adjustable straps fastened by a Velcro type fastener.

SUMMARY OF THE INVENTION

A hand restraining device including a rigid support member and a plurality of straps for securing the hand, fingers and, preferably, the wrist and forearm of an individual to this support member. The support member includes a hand portion and at least 2 finger portions. Preferably a third finger portion is included and the hand portion is elongated to extend under the wrist and forearm. The straps hold, respectively, the thumb to one of the finger portions, the baby finger to the other of the finger portions, the three middle fingers and the hand flat against the front surface of the support member. Supported on the strap which holds the three middle fingers is a rigid restraining piece which is used to prevent the user from bending his/her knuckles. Preferably each of the straps, except the wrist strap, is secured at one end to an elongated slot provided in the support member, which slot permits lateral positioning of such strap. The opposite end of the strap is, preferably, secured to the back of the support member by a Velcro fastener or equivalent.

Preferably the hand restraining device is used to hold the hand of an infant or toddler flat, with the palm in contact with the top surface of the support member, so that the infant's nails are exposed for clipping, trimming, etc.

BRIEF DESCRIPTION OF THE DRAWINGS

FIG. 1 is the top view of the preferred embodiment of the present invention;

FIG. 2 is the front view of the apparatus of FIG. 1;

FIG. 3 is a side view of the apparatus of FIG. 2;

FIG. 4 is the back view of the apparatus of FIG. 2;

FIG. 5 is the bottom view of the apparatus of FIG. 2;

FIG. 6 is a top perspective view of the preferred embodiment; and

FIG. 7 is a bottom perspective view of the preferred embodiment.

DESCRIPTION OF THE PREFERRED EMBODIMENT

The hand restraining device 11 of the present invention consists of a support member 13 and, preferably, five restraining straps, 15, 17, 19, 21 and 23 which are used to secure an infant's (or toddler's) hand (not-shown) to the front surface 25 of support 13. Supported on strap 21, is a ridged knuckle restraining piece 27 to prevent the user from bending his/her knuckles.

As shown in, particularly, FIGS. 2 and 6, support 13 includes a wrist/forearm portion 31, a first thumb/baby finger portion 33, a second thumb/baby finger portion 35, and a middle finger portion 37. Support 13 includes the back surface 39 (see FIGS. 4 and 7), and edge 40 and a plurality of slots 41, 43, 45, 47 and 49 for the attachment of, respectively, straps 15, 17, 19, 21 and 23. Support 13 is made of molded plastic material such as polycarbonate or nylon. However, other suitable ridged materials and other manufacturing techniques can be substituted. For use with an infant, a thickness of 3/32 of an inch has been found to be adequate. The preferred embodiment, support 13 is dimensioned to fit infants and toddlers from, approximately 4 months to two and a half years of age.

Straps 15, 17, 19, 21 and 23 are, preferably, a form of standard loop Velcro. With reference to, for instance, strap 15, one end is looped around the support web 51 between slot 41 and edge 40 of support 13 and sewn together, as illustrated in at 53 FIG. 6. The opposite, or free end of strap 15 is attachable to the back surface 39 of support 13 by a pad 61 of PSA hook Velcro which is glued or otherwise bonded to surface 39. The length of strap 15 is sufficient to secure the forearm of various thicknesses to front surface 25 of support 13. The length of slot 41 permits strap 15 to be laterally adjusted to the most appropriate location for securing a particular infants forearm (not shown). Similarly, straps 17, 19, 21 and 23 are secured at one of their respective ends to slots 43, 45, 47 and 49 in the same manner as strap 15 is secured to slot 41. Further, straps 17, 19, 21 and 23 are secured to back surface 39 by pads, of PSA hook Velcro, 63, 65, 67 and 69. Like slot 41, slots 45, 47 and 49 are elongated to permit lateral adjustment. In the preferred embodiment, straps 15, 17 and 21 are, approximately, 5/8 inch wide; straps 19 and 23 are preferably approximately 3/8 inch wide. The lengths are sufficient to accommodate wrists, forearms and fingers of various thickness.

Ridged member 27 has two slots 71 and 73 through which strap 21 is threaded. Member 27 provides rigidity to insure that the middle fingers of the infant are held flush against front surface 39 of support 13 to prevent such fingers from being curled up which would, for instance, prevent the nails on an infant's fingers from being properly clipped.

In operation, the infant's hand (not shown) is placed palm down on the front surface 25 of support 13 and held flush against surface 25 by straps 15, 17, 19, 21 and 23, which are wrapped firmly around the infants forearm, wrist, thumb, baby finger and middle fingers, and then secured to pads 61, 63, 65, 67 and 69. When so positioned, the infants fingernails are exposed and positioned for easy clipping or other activity.

Whereas, the drawings and accompanying description have shown and described the preferred embodiment of the present invention, it should be apparent to those skilled in the art that various changes may be made in the form of the invention without affecting the scope thereof. For instance, the present invention need not be restricted for the use of infants and toddlers, but may also be used with newborns, adolescents and adults, not only for the purpose of the present invention but other medical and/or surgical purposes.

What I claim is:

1. A hand restraint apparatus comprising:
   a. a rigid support including, a main portion and at least two finger portions, said portions having front and back surfaces;
   b. means for securing at least the wrist, hand and fingers of an individual to said support, said securing means including a plurability of straps, one for holding the wrist of an individual in contact with said front surface of said main portion, a second strap for holding the thumb of said individual in contact with said front surface of one of said finger portions, a third strap for holding the baby finger of said individual in contact with said front surface of the other of said finger portions, and a fourth strap for holding the middle fingers of said individual in contact with said front surface of main portion; and
   c. a rigid member secured to said fourth strap which, is use, presses against and holds said middle fingers flush against said front surface of said main portion.

2. The apparatus of claim 1, wherein said support has at least one slot and wherein at least one of said straps is secured at one end to said slot provided in said support, whereby the position of said at least one strap is adjustable along the length of said support.

3. The apparatus of claim 1 further including a fifth strap for holding the forearm of said individual in contact with said front surface of said main portion.

4. The apparatus as set forth in claim 1, wherein said straps include hook and loop type means for securing the free end of said straps to said support.

* * * * *